US012797121B2

(12) United States Patent
Thom et al.

(10) Patent No.: US 12,797,121 B2
(45) Date of Patent: Nov. 17, 2026

(54) COMBINATION RF AND MICROWAVE ENERGY ABLATION DEVICE

(71) Applicant: Neuwave Medical, Inc., Madison, WI (US)

(72) Inventors: Mark Thom, Verona, WI (US); Matthew J. Thiel, Verona, WI (US)

(73) Assignee: Neuwave Medical, Inc., Madison, WI (US)

( * ) Notice: Subject to any disclaimer, the term of this patent is extended or adjusted under 35 U.S.C. 154(b) by 158 days.

(21) Appl. No.: 18/926,936

(22) Filed: Oct. 25, 2024

(65) Prior Publication Data

US 2026/0114917 A1 Apr. 30, 2026

(51) Int. Cl.

*A61B 18/14* (2006.01)
*A61B 18/00* (2006.01)
*A61B 18/18* (2006.01)

(52) U.S. Cl.

CPC *A61B 18/1477* (2013.01); *A61B 2018/00077* (2013.01); *A61B 2018/00083* (2013.01); *A61B 2018/00702* (2013.01); *A61B 2018/00958* (2013.01); *A61B 2018/00994* (2013.01); *A61B 2018/1869* (2013.01)

(58) Field of Classification Search

CPC ...... A61B 18/1477; A61B 2018/00077; A61B 2018/00083; A61B 2018/00702; A61B 2018/00958; A61B 2018/00994; A61B 2018/1869

See application file for complete search history.

(56) References Cited

U.S. PATENT DOCUMENTS 11,389,235 B2 7/2022 Van Der Weide et al.
2015/0133910 A1* 5/2015 Brannan ............ A61B 18/1815 606/33
2020/0179653 A1* 6/2020 Hancock .............. A61B 1/0058
2021/0196376 A1* 7/2021 Hancock ................ A61B 1/005

* cited by examiner

*Primary Examiner* — Khadijeh A Vahdat

(74) *Attorney, Agent, or Firm* — Troutman Pepper Locke LLP; Scott D. Wofsy; Michael J. Pollack

(57) ABSTRACT

An energy delivery device is disclosed that includes an antenna that is operable in a first mode in which the antenna provides microwave energy to tissue and a second mode in which the antenna provides radiofrequency (RF) energy to tissue.

8 Claims, 5 Drawing Sheets

COMBINATION RF AND MICROWAVE ENERGY ABLATION DEVICE

BACKGROUND

Ablation is an important therapeutic strategy for treating certain tissues, such as benign and malignant tumors, cardiac arrhythmias, cardiac dysrhythmias, and tachycardia. Some ablation systems utilize radio frequency (RF) energy as the ablating energy source. RF energy is particularly advantageous as tissue can be heated quickly and can be delivered using regular conductive wires. However, RF energy has several limitations, including the rapid dissipation of energy in surface tissues, resulting in shallow "burns" and failure to access deeper tumor or arrhythmic tissues. Another limitation of RF ablation systems is the tendency of eschar and clot formation on the energy emitting electrodes, which limits further deposition of electrical energy.

More recently, microwave energy has been used as the ablating energy source in ablation systems. Microwave energy is an effective energy source for heating biological tissues and is used in applications such as cancer treatment and preheating of blood prior to infusions. One advantage of microwave energy is deep penetration into tissue, insensitivity to charring, lack of necessity for grounding, more reliable energy deposition, faster tissue heating, and the capability to produce much larger thermal lesions when compared to RF energy, which greatly simplifies the actual ablation procedures.

Despite the foregoing advantages provided by using microwave energy, it may still be advantageous to utilize RF energy in certain circumstances. For instance, during a surgical procedure, a surgeon utilizing a microwave ablation device may desire to provide precise, localized heating to tissue, which may be best accomplished with RF energy. Current practice would require the surgeon to remove the microwave ablation device from the patient and introduce an RF ablation device into the patient. However, a substitution of instruments mid-procedures may not be practical considering the amount of time that is required to accurately place the devices prior to providing energy to the tissue.

Accordingly, there is a need for improved systems and methods for providing both RF and microwave energy to patient tissue during a surgical procedure.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to systems and methods for delivering energy to tissue for an ablation operation and, more particularly, to systems and methods for delivering RF and microwave energy to tissue with a single instrument.

The present disclosure is related to comprehensive systems, devices, and methods for delivering energy (e.g., microwave energy, radiofrequency energy, laser, focused ultrasound, plasma, etc.) to tissue for a wide variety of applications including medical procedures (e.g., percutaneous or surgical). Example medical procedures that may benefit from the embodiments described herein include, but are not limited to, tissue ablation, resection, cautery, vascular thrombosis, intraluminal ablation of a hollow viscus, cardiac ablation for treatment of arrhythmias, electrosurgery, tissue harvest, cosmetic surgery, intraocular use, or any combination thereof.

More specifically, the present disclosure is related to a single energy delivery device that can provide both RF and microwave energy to patient tissue. The energy delivery device can be use in two modes—an RF mode, in which the energy delivery device is placed in electrical communication with an RF generator to generate an RF ablation zone, and a microwave mode, in which the energy delivery device is placed in electrical communication with a microwave generator to generate a microwave ablation zone.

Figure 1:
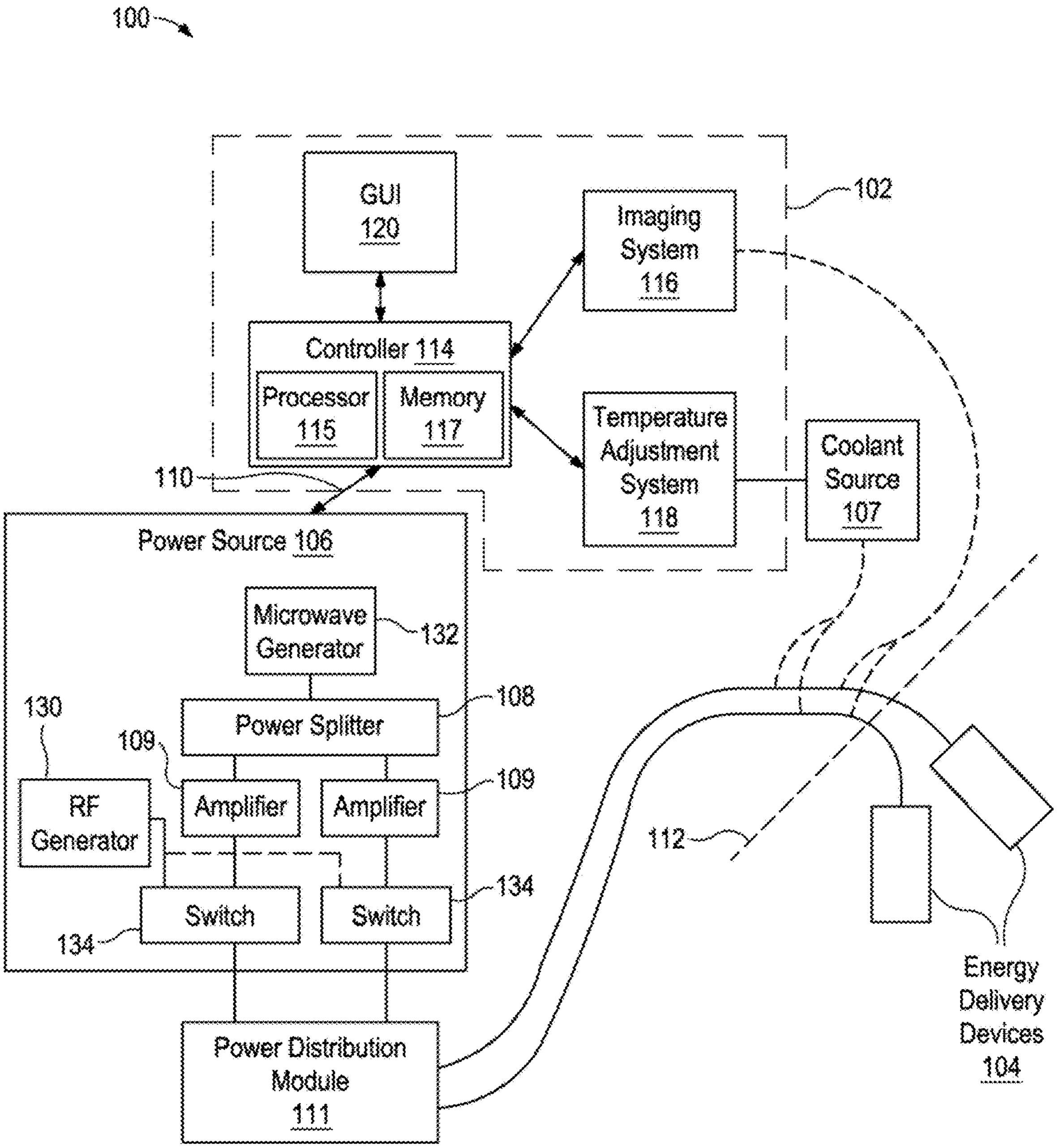
FIG. 1 is a block diagram of an example energy delivery system that may be used in accordance with the principles of the present disclosure.

FIG. 1 is a block diagram of an energy delivery system 100, according to at least one aspect of the present disclosure. As illustrated, the energy delivery system 100 (hereafter "the system 100") includes a control system 102 and one or more energy delivery devices or "ablation probes" 104 (two shown) designed to deliver (emit) energy (e.g., microwave energy or radiofrequency energy) to a target tissue region of a patient. While two ablation probes 104 are shown, the system 100 may include only one ablation probe 104 or more than two ablation probes 104 (e.g. three, four, or five ablation probes).

The system 100 further includes a power source 106 communicably coupled to the control system 102 and the ablation probes 104. The power source 106 is operable direct, control, and deliver (provide) electrical power to the ablation probes 104. In some applications, the power source 106 may include an RF generator 130 and a microwave generator 132. The RF generator 130 may be operable to deliver energy at a frequency of about 480 kHz and the microwave generator 132 may be operable to deliver energy at a frequency of about 2.45 GHZ. The power source 106 may receive power from an external power source (e.g. a wall outlet) to power the RF and microwave generators 130, 132.

The power source 106 may further include a power splitter 108 that may direct the received energy from the microwave generator 132 to one or more amplifiers 109 (two shown), each of which amplifies the voltage, current, or power from the power splitter 108 to an associated ablation probe 104. While two amplifiers 109 are shown, each associated with a corresponding ablation probe 104, the power source 106 may include less than two amplifiers (e.g. one amplifier) or more than two amplifiers (e.g. three, four, or five amplifiers, for example).

The power source 106 may further include one or more switches 134 that may receive microwave energy from a corresponding amplifier 109 and RF energy from the RF generator 130. In some embodiments, as illustrated, the power source 106 may include a single RF generator 130 that feeds multiple switches 134. In other embodiments, the power source 106 may include more than one RF generators 130 with each switch 134 operable to receive energy from a dedicated RF generator 130.

Each switch 134 may be transitionable between a first or "microwave" state and a second or "RF" state. In the microwave state, the switch 134 may place the associated amplifier 109 in electrical communication with the associated ablation probe 104 and electrically disconnect the RF generator 130 from the associated ablation probe 104. Accordingly, in the microwave state, the ablation probe 104 may receive microwave energy from the power source 106. In the RF state, the switch 134 may place the RF generator 130 in electrical communication with the associated ablation probe 104 and electrically disconnect the amplifier 109 from the associated ablation probe 104. Accordingly, in the RF state, the ablation probe 104 may receive RF energy from the power source 106.

Each switch 134 may be coupled to a corresponding ablation probe 104 via a power distribution module 111, which provides strain relief to the cabling extending from the switches 134 to the ablation probes 104. The power distribution module 111 may be coupled to a structure in the operating room, such as a surgical bed, and may house connection hardware of the probes 104.

The components of the system 100 are connected via one or more cables or transmission lines 110. Moreover, the ablation probes 104 are designed to operate within a sterile field facilitated by the use of a sterile field barrier 112 that separates the ablation probes 104 from the remaining components of the system 100. The sterile field barrier 112 creates the sterile field, which includes any region permitting access only to sterilized items (e.g., sterilized devices, sterilized accessory agents, sterilized body parts, etc.). The sterile field barrier 112 hinders entry of non-sterile items into the sterile field, and the ablation probes 104 are configured for operation within the sterile field.

The control system 102 is configured to monitor, control, and provide feedback concerning operation of the system 100. As illustrated, the control system 102 includes at least a controller 114, an imaging system 116, and a temperature adjustment system 118. The control system 102 may further include a graphical user interface (GUI) or display 120, such as a touchscreen interface, which can be accessed by a user (e.g., a surgeon, a nurse, bedside assist, etc.) to operate the system 100. For instance, a user may provide an input to the display 120 to transition the switch 134 between the microwave and RF states. In some applications, the control system 102 may be mounted to or otherwise form part of a portable cart or "procedure cart," and the GUI 120 may be arranged in a display region for operating and/or monitoring the components of the system 100.

The controller 114 may include a processor 115 and a memory or memory device 117 comprising any storage media readable by the processor 115. The memory 117 may store software or software instructions executable by the processor 115 to carry out functions and operations of the system 100. Examples of the memory 117 include, but are not limited to, random access memory (RAM), read-only memory (ROM), computer chips, optical discs (e.g., compact discs (CDs), digital video discs (DVDs), etc.), magnetic disks (e.g., hard disk drives (HDDs), floppy disks, ZIP® disks, etc.), magnetic tape, and solid state storage devices (e.g., memory cards, "flash" media, etc.). As used herein, the term "computer readable medium" refers to any device or system for storing and providing information (e.g., data and instructions) to the processor 115. Examples of computer readable media include, but are not limited to, optical discs, magnetic disks, magnetic tape, solid-state media, and servers for streaming media over networks.

Based on instructions provided by the software, the controller 114 may be configured to regulate the amount of energy (e.g., RF or microwave energy from the RF and microwave generators 130, 132, respectively) provided to a tissue region by the ablation probes 104 by monitoring characteristics of the tissue region, such as the size and shape of a target tissue, the temperature of the tissue region, etc. The controller 114 may interact with the ablation probes 104 to raise or lower (e.g., tune) the amount of energy delivered to the tissue region. The controller 114 may also be configured to prime coolants for distribution into the ablation probes 104 such that the coolant is delivered at a desired temperature.

In some applications, the type of tissue being treated is inputted into the software for purposes of allowing the controller 114 to regulate (e.g., tune) the delivery of RF and/or microwave energy to the tissue region based upon pre-calibrated methods for that particular type of tissue or tissue region. In other embodiments, however, the type of probe selected for the particular procedure may be specifically tuned to a specific tissue type, and projected (expected) ablation sizes may be based on tissue type. In such embodiments, the controller 114 may not control power delivery based on tissue type. In yet other embodiments, the controller 114 generates a chart or diagram based upon a particular type of tissue or tissue region displaying characteristics useful to a user of the system.

The controller 114 may allow a user to choose a type of power (RF or microwave), a power level, duration of treatment, different treatment algorithms for different tissue types, simultaneous application of power to multiple probes 104, coherent and incoherent phasing, etc. The controller 114 may also be configured to create a database of information (e.g., required energy levels, duration of treatment for a tissue region based on particular patient characteristics, etc.) pertaining to ablation treatments for a particular tissue region based upon previous treatments with similar or dissimilar patient characteristics.

The control system 102 further includes the imaging system 116, which may be in communication with the controller 114 and comprises one or more imaging devices. Example imaging devices include, but are not limited to, endoscopic devices, stereotactic computer assisted neurosurgical navigation devices, thermal sensor positioning systems, motion rate sensors, steering wire systems, intraprocedural ultrasound, interstitial ultrasound, microwave imaging, acoustic tomography, dual energy imaging, fluoroscopy, computerized tomography magnetic resonance imaging, nuclear medicine imaging devices triangulation imaging, thermoacoustic imaging, infrared and/or laser imaging, or electromagnetic imaging. In some embodiments, the system 100 uses endoscopic cameras, imaging components, and/or navigation systems that permit or assist in placement, positioning, and/or monitoring of the ablation probes 104.

Figure 2:
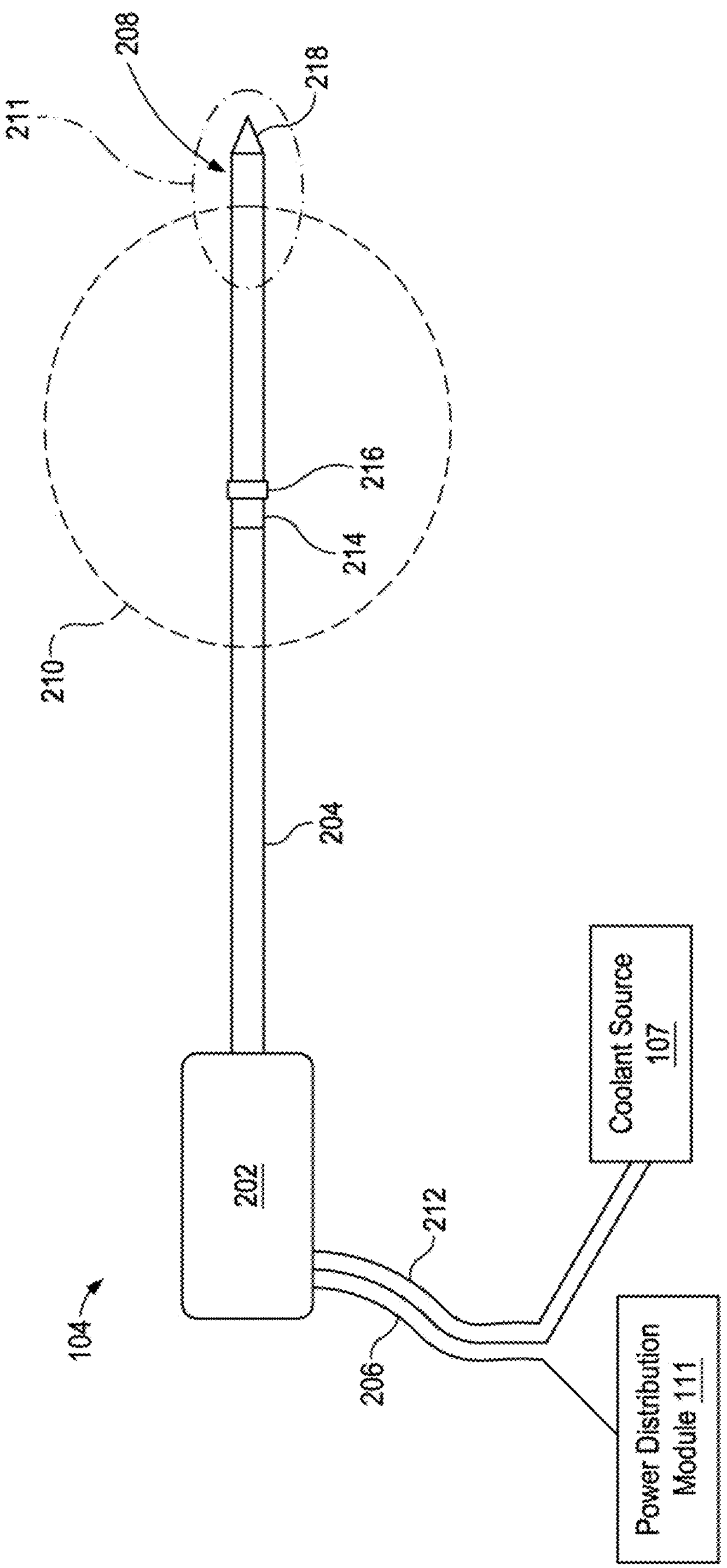
FIG. 2 is a schematic diagram of an ablation probe of FIG. 1 with an antenna for generating a microwave ablation zone and an RF ablation zone, according to at least one aspect of the present disclosure.

In some applications, the system 100 may provide software configured for use with imaging equipment of the imaging system 116, such as CT, MRI, and ultrasound, and generate two-dimensional (2D) and or three-dimensional (3D) images viewable by a user on the GUI 120. In some embodiments, the imaging equipment software allows a user to make predictions based upon known thermodynamic and electrical properties of tissue, vasculature, and location of the antenna(s) 208 (FIG. 2). In some embodiments, the imaging software allows the generation of a 2D or 3D map of the location of a tissue region (e.g., tumor, arrhythmia), location of the antenna(s) 208 (FIG. 2), and to generate a predicted map of the ablation zones 210, 211 (FIG. 2).

In some applications, the imaging system 116 may be configured to monitor ablation procedures, such as monitoring the amount of ablation occurring within a particular tissue region(s) undergoing a thermal ablation procedure. The monitoring includes, but is not limited to, MRI imaging, CT imaging, ultrasound imaging, nuclear medicine imaging, and fluoroscopy imaging. The software may be designed to automatically obtain images of a tissue region (e.g., MRI imaging, CT imaging, ultrasound imaging, nuclear medicine imaging, fluoroscopy imaging), automatically detect any changes in the tissue region (e.g., blood perfusion, temperature, amount of necrotic tissue, etc.), and based on the detection to automatically adjust the amount of energy delivered to the tissue region through the ablation probes 104.

The temperature adjustment system 118 may be configured to use coolant systems and cooling fluids to help reduce undesired heating within and along the ablation probes 104. In particular, the temperature adjustment system 118 may include a coolant source 107 and control conveyance of cooling fluid or "coolant" from the coolant source 107 to the ablation probes 104, as discussed in more detail below. Example cooling fluids include, but are not limited to, water, glycol, air, inert gases (e.g., helium), carbon dioxide, nitrogen, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide, or any combination thereof.

The temperature adjustment system 118 may also be configured to continuously or intermittently monitor the real-time temperature of the ablation probes 104. In such embodiments, the temperature adjustment system 118 may communicate with one or more temperature sensors (e.g., thermocouples) terminating at various points along the ablations probe 104, such as a probe cannula 204 (FIG. 2) and/or an antenna 208 (FIG. 2) of the ablation probe 104. Consequently, localized temperature may be monitored at several points along the ablation probe 104 to estimate ablation status, cooling status, or safety checks. In some applications, monitoring the temperature at several points along the ablation probe 104 may help determine the geographical characteristics of generated ablation zones, such as the diameter, depth, length, density, width, etc., based upon the tissue type, and the amount of power used in the ablation probe 104. In other embodiments, or in addition thereto, the temperature may be measured not only at specific points along the probe cannula 204, but continuously along its entire length.

The temperature adjustment system 118 may also be configured to monitor the temperature of a tissue region (e.g., tissue being treated, surrounding tissue). This may prove advantageous in helping to determine the status of the procedure (e.g., the end of the procedure). The temperature adjustment system 118 may communicate with the controller 114 to provide real-time temperature information to a user and display such measurements on the GUI 120. In at least one embodiment, based on the temperature data obtained by the temperature adjustment system 118, the controller 114 may be configured to autonomously adjust operation of the system 100 appropriately.

FIG. 2 is a schematic diagram of one of the ablation probes 104 of FIG. 1, in accordance with at least one aspect of the present disclosure. As indicated above, the ablation probe 104 may be configured to deliver (emit) energy (e.g., microwave energy or radiofrequency energy) to a target tissue region. As illustrated, the ablation probe 104 includes a handle housing 202 and an elongate shaft or probe cannula 204 extending distally from the handle housing 202.

A cable or cable assembly 206 may be operatively coupled to the handle 202 and configured to convey electrical energy thereto. The cable assembly 206 may extend from the power distribution module 111 (FIG. 1), for example, and may provide the power sufficient to operate the ablation probe 104. An antenna 208 may be provided at a distal end of the probe cannula 204 and may receive electrical energy (e.g., RF or microwave energy from the RF or microwave generators 130, 132, respectively) from the cable assembly 206. Upon receiving microwave energy, the antenna 208 is configured to generate a microwave ablation zone 210 (shown in dashed lines) to a target tissue region, as discussed in more detail below. Upon receiving RF energy, the antenna 208 is configured to generate an RF ablation zone 211 (shown in dot-dashed lines) to a target tissue region, as also discussed in more detail below.

In some applications, a cooling conduit or tube 212 is operatively coupled and configured to convey the coolant from the coolant source 107 to the handle 202. The handle 202 may be configured to control conveyance of the cooling fluid into and out of the probe cannula 204 to help regulate a temperature of the antenna 208 and the ablation zones 210, 211.

In some applications, the ablation probe 104 may include a stick region 214, alternately referred to as a "tissue-loc" region, provided on the probe cannula at or near the antenna 208. The stick region 214 is designed to attain and maintain a temperature that accommodates adherence of a tissue region onto its surface. More specifically, the stick region 214 may operate as an anchoring element having a circulating agent or "coolant" (e.g., a gas delivered at or near its critical point; $CO_2$) that freezes the interface between the stick region 214 and the adjacent tissue, thereby sticking (maintaining, locking, etc.) the antenna 208 in place during operation. The coolant may be provided to the stick region 214 via the cooling tube 212 from the coolant source 107, for example. Once a pre-determined low temperature is reached at the stick region 214, contact with adjacent tissue causes the tissue to adhere to the stick region 214, thereby resulting in attachment of the energy delivery device 104 to the tissue. During ablation, and as the tissue warms, the antenna 208 remains secured to the tissue region due to tissue desiccation and charring.

In some applications, the temperature adjustment system 118 may be configured to communicate with the handle 202 to operate the stick region 214 and thereby attain and maintain a temperature that accommodates adherence of tissue onto its surface. For instance, in some embodiments, a user provides an input to an input interface, such as the GUI 120. Based on the user input, the temperature adjustment system 118 may control the coolant source 107 to provide coolant to the stick region 214, thereby adhering the stick region 214 to the adjacent tissue.

The stick region 214 may be made of any material able to attain and maintain a temperature such that upon contact with tissue induces adherence of the tissue onto the stick region 214. An example material for the stick region 214 includes, but is not limited to, a metal.

In some applications, the ablation probe 104 may further include a plug region 216 provided on the probe cannula 204 at or near the antenna 208. In at least one application, as depicted, the plug region 216 may be provided distal to the stick region 214 and otherwise interposing the stick region 214 and the antenna 208. The plug region 216 may be configured to prevent a reduction in temperature resulting from the cooled probe cannula 204 and the stick region 214 from affecting (e.g., reducing) the temperature within the antenna 208. Accordingly, the plug region 216 separates interior portions of the ablation probe 104 to prevent cooling or heating of a portion or portions of the probe 104 while permitting cooling or heating of other portions. The plug region 216 may be made of an insulative material capable of being in contact with a material or region having a low temperature without having its temperature significantly reduced. Example insulative materials for the plug region 216 include, but are not limited to, a synthetic polymer (e.g., polystyrene, polyicynene, polyurethane, polyisocyanurate), aerogel, fiberglass, cork, or any combination thereof.

In some applications, the ablation probe 104 may further include a sharp stylet tip or "stylet" 218 positioned at the distal end of the antenna 208 and otherwise forming the distal end of the ablation probe 104. The stylet 218 may be designed to facilitate percutaneous insertion of the ablation probe 104. The stylet 218 may be made of a variety of rigid or hardened materials including, but not limited to, a hardened resin, a conductive metal (e.g., titanium or an equivalent of titanium, stainless steel, etc.), a ceramic, or any combination thereof. In at least one application, the stylet 218 may be brazed to zirconia or an equivalent of zirconia. In such applications, the stylet 218 may comprise an extension of a metal portion of the antenna 208 and may be electrically active.

In some applications, the ablation probe 104 may have a coaxial transmission line positioned within the antenna 208, and a coaxial transmission line connecting with the antenna 208. In other embodiments, the ablation probe 104 may comprise a triaxial microwave probe with optimized tuning capabilities. The ablation probe 104 may be the same as or similar to any of the energy delivery devices described in U.S. Pat. No. 11,638,607, entitled "ENERGY DELIVERY SYSTEMS AND USES THEREOF", which issued on May 2, 2023, the contents of which are hereby incorporated by reference in their entirety herein.

In some embodiments, the probe cannula 204 includes a plurality of temperature sensors. A first temperature sensor may be placed at, or slightly proximal to, the antenna 208 to provide real-temperature measurements of the tissue being heated by the antenna 208. A second temperature sensor may be placed at, or adjacent to, the stick region 214 to provide real-time temperature measurements of the tissue that is being cooled, and thus adhered to, the stick region 214. A third temperature sensor may be located proximal to the first and second temperature sensors along the cannula 204, such as at the point of entry into the skin, to provide real-time measurements of the patent's skin. The control system 102 may receive the temperature measurements from the first, second, and third sensors to control the coolant systems and cooling fluids from the temperature adjustment system 118 to the stick region 214 and/or other cooling systems of the energy delivery device 104, as will be described in more detail below.

Figure 3:
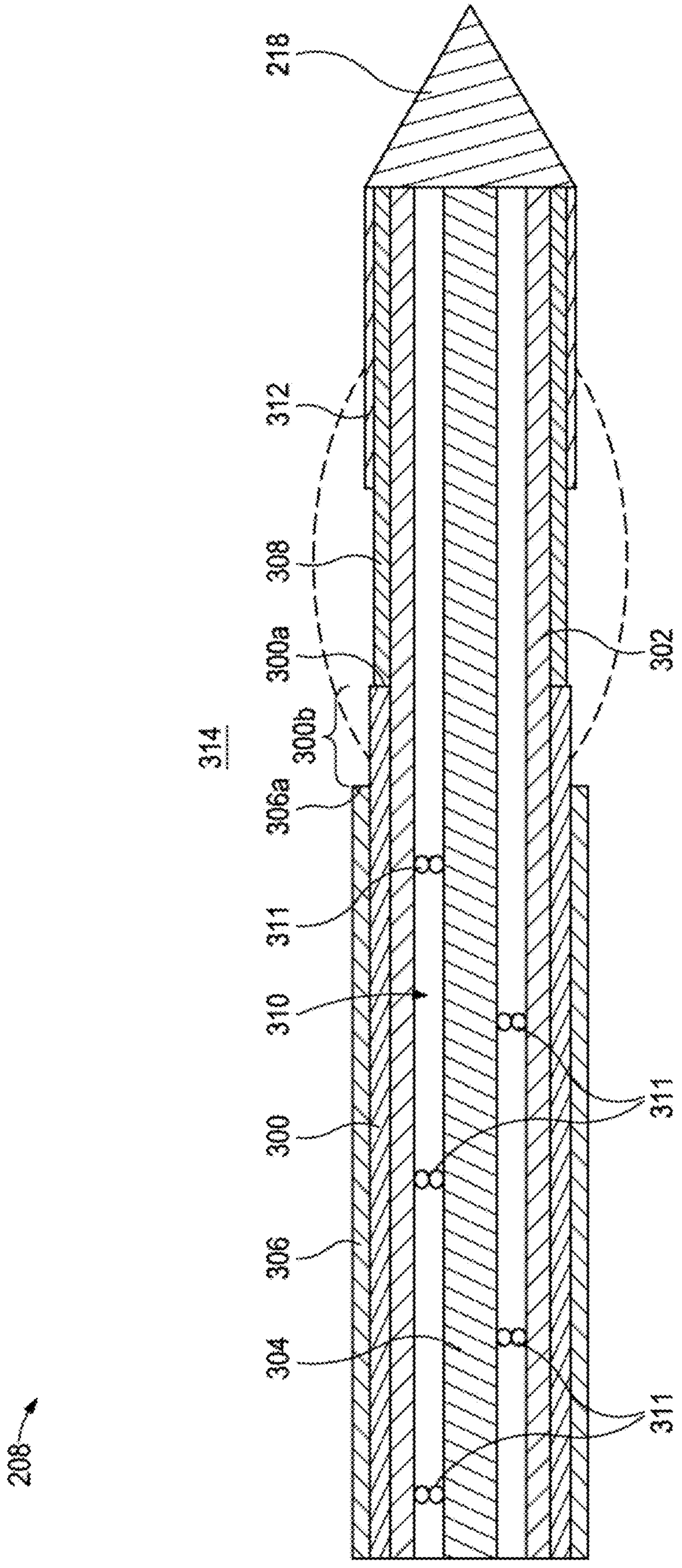
FIG. 3 is an enlarged, cross-sectional view of the antenna of FIG. 2, according to at least one aspect of the present disclosure.

FIG. 3 is an enlarged, cross-sectional view of the antenna 208 of FIG. 2, according to at least one aspect of the present disclosure. As illustrated, the antenna 208 may include a coaxial cable arrangement for delivering both microwave and RF energy to tissue. More specifically, the antenna 208 may include an outer conductor 300, a dielectric tube 302 extending within an interior of the outer conductor 300, and an inner conductor 304 extending within an interior of the dielectric tube 302.

The antenna 208 may further include a first insulation tube 306 positioned about (around) the outer conductor 300. As illustrated, a distal end 306*a* of the first insulation tube 306 may be located proximal to a distal end 300*a* of the outer conductor 300 such that a portion 300*b* of the outer conductor 300 is exposed and otherwise uncovered by the first insulation tube 306. The antenna 208 may further include a second insulation tube 308 extending from the distal end 300*a* of the outer conductor 300 to the stylet 218, and may be positioned about (around) the dielectric tube 302.

The outer conductor 300 may be made of a conductive material that allows current to be transmitted along a length thereof. The outer conductor 300 may be made of a metal, for example, such as stainless steel, silver, copper, brass or aluminum, or alloys thereof. In some embodiments, the outer conductor 300 extends from the plug region 216 (FIG. 2). In at least one embodiment, the outer conductor 300 may comprise a 15 gauge hypotube.

The dielectric tube 302 may extend through (within) the outer conductor 300 and may be arranged concentric therewith. The dielectric tube 302 may be made of a polymer, such as polyamide, linear polyethylene (PE), polyethylene terephthalate (PET), polytetrafluoroethylene (PTFE) isotactic polypropylene (PP), or a polymer in the polyaryletherketone (PAEK) family, such as polyetheretherketone (PEEK), as examples.

The inner conductor 304 may extend through (within) the dielectric tube 302 and may be arranged concentric therewith. The inner conductor 304 may be made of a conductive material that allows current to be transmitted along a length thereof. The inner conductor 304 may be made of a metal, for example, such as stainless steel, silver, copper, brass or aluminum, or alloys thereof.

As illustrated, an air gap 310 may be defined between the dielectric tube 302 and the inner conductor 304. One or more spacers 311 may be positioned in the air gap 310 to maintain a spacing between the dielectric tube 302 and the inner conductor 304. In some embodiments, the spacers 311 may comprise monofilament tubing separating and spacing the dielectric tube 302 from the inner conductor 304. In other embodiments, or in addition thereto, the spacers 311 may comprise one or more tubes that are helically wrapped around the inner conductor 304. The tubes may be made of any desired material, such as a non-conductive material, like plastic or perfluoroalkoxy alkane (PFA).

The antenna 208 may further include an electrode 312 that may be tubular and positioned about (around) the second insulation tube 308. The electrode 312 may also be electrically coupled with the stylet 218. In some embodiments, the electrode 312 and the stylet 218 may be integrally constructed (formed), such as on a lathe from a piece of stock metal. In such embodiments, the electrode 312 and the stylet 218 may be made of the same material such as, but not limited to, stainless steel, silver, copper, brass or aluminum, alloys thereof, or any combination thereof. In other embodiments, however, the electrode 312 and the stylet 218 may be separate component parts that are operatively coupled (e.g., welded, mechanically fastened, etc.). In such embodiments, the material of the electrode 312 and the stylet 218 may be the same or different. As one example, the electrode 312 may be made of copper and the stylet 218 may be made of brass.

The inner conductor 304 and the stylet 218 may be integrally constructed (formed), such as on a lathe from a piece of stock metal. In such embodiments, the inner conductor 304 and the stylet 218 may be made of the same material including, but not limited to, stainless steel, silver, copper, brass or aluminum, alloys thereof, or any combination thereof. In other embodiments, however, the inner conductor 304 and the stylet 218 may comprise separate component parts that are operatively coupled (e.g., welded, mechanically fastened, etc.). In such embodiments, the material of the inner conductor 304 and the stylet 218 may be the same or different. As one example, the inner conductor 304 may be made of copper and the stylet 218 may be made of brass.

The inner conductor 304 may be in electrical communication with the stylet 218 such that a current supplied to the inner conductor 304 may be transmitted to the electrode 312 via the stylet 218. In some embodiments, the inner conductor 304, the stylet 218, and the electrode 312 are all integrally constructed. In other embodiments, however, the inner conductor 304, the stylet 218, and the electrode 312 may each comprise separate component parts that are operatively coupled.

As referenced above, the antenna 208 is configured to deliver microwave or RF energy to tissue. The antenna 208 may be used in a first or "microwave" mode in which the antenna 208 provides microwave energy to tissue to generate the microwave ablation zone 210 (FIG. 2). More specifically, with reference to FIGS. 1-3, a user may desire to provide microwave energy to tissue 314. Accordingly, a user may provide a first input to the controller 114 via the GUI 120, and the controller 114 may place the switch 134 in the microwave state, as discussed elsewhere herein.

A user may then provide a second input to the controller 114 via the GUI 120. Based on receiving the second input, the controller 114 may cause the microwave generator 132 to provide microwave energy to the inner conductor 304 via the switch 134. The microwave energy may be delivered along the inner conductor 304 to the stylet 218 and the electrode 312, and may be emitted from the inner conductor 304, the stylet 218, and the electrode 312 to generate the microwave ablation zone 210.

The stylet 218 and/or the electrode 312 may serve as a load point and may include longitudinal lengths that are tuned to match the dielectric properties of the surrounding tissue, which may contribute to the ability of the antenna 208 to generate a spherical ablation zone, which may be more preferred than a typical ellipsoid or "tear drop" shaped ablation zone. More details regarding spherical ablation zones are provided in U.S. patent application Ser. No. 18/810,315, titled "COOLED ANTENNAS FOR SPHERICAL ABLATION", filed Aug. 20, 2024, which is hereby incorporated by reference in its entirety herein.

The antenna 208 may also be used in a second or "RF" mode in which the antenna 208 provides bipolar RF energy to tissue to generate an RF ablation zone 211 (FIG. 2). In the RF mode, the inner conductor 304, the stylet 218, and the electrode 312 may serve as a portion of a supply path and the outer conductor 300 may serve as a portion of the return path. More specifically, with continued reference to FIGS. 1-3, in operation, a user may desire to provide bipolar RF energy to tissue, such as after providing microwave energy to tissue, as described above. Accordingly, a user may provide a third input to the controller 114 via the GUI 120. Based on receiving the third input, the controller 114 may transition the switch 134 from the microwave state to the RF state, as discussed elsewhere herein.

A user may then provide a fourth input to the controller 114 via the GUI 120. Based on receiving the fourth input, the controller 114 may cause the RF generator 130 to provide RF energy to the inner conductor 304 via the switch 134. The RF energy may be delivered along the inner conductor 304 to the stylet 218 and the electrode 312. The RF energy may then be delivered to the exposed portion **300*b* of the outer conductor 300 via tissue 314 surrounding the antenna 208, as shown with the dashed lines extending between the electrode 312 and exposed portion 300*b* in FIG. 2. The RF energy may then be delivered along the outer conductor 300 as a return path. Accordingly, the foregoing bipolar RF energy delivery produces (generates) the RF ablation zone 211 (FIG. 2**).

Accordingly, a user can selectively apply RF and microwave energy to patient tissue by simply switching the antenna 208 back and forth between the RF and microwave modes, such as by providing an input to the GUI 120 to transition the switch 134 between the RF and microwave states, respectively. It should be understood that the antenna 208 may be transitioned back and forth between the microwave and RF modes as desired by the user.

In some embodiments, the controller 104 may automatically control the power source 106 to provide energy to the tissue 314. For instance, a user may desire to provide both RF and microwave energy to tissue 314. Accordingly, a user may provide an input to the controller 114 via the GUI 120. Based on receiving the input, the controller 114 may automatically control the power source 106 to provide RF and microwave energy to the ablation probe 104. For example, the controller 114 may cause the power source 106 to provide RF energy for a first amount of time and then microwave energy from a second amount of time. As another example, the controller 114 may cause the power source 106 to alternate between providing RF and microwave energy based on a desired tissue effect or operating mode of the ablation probe. The memory 117 may store an algorithm which may provide instructions on how to automatically control the power source 106 and the algorithm may be retrievable by the controller 114 based on the controller receiving the user input via the GUI.

Figure 4:
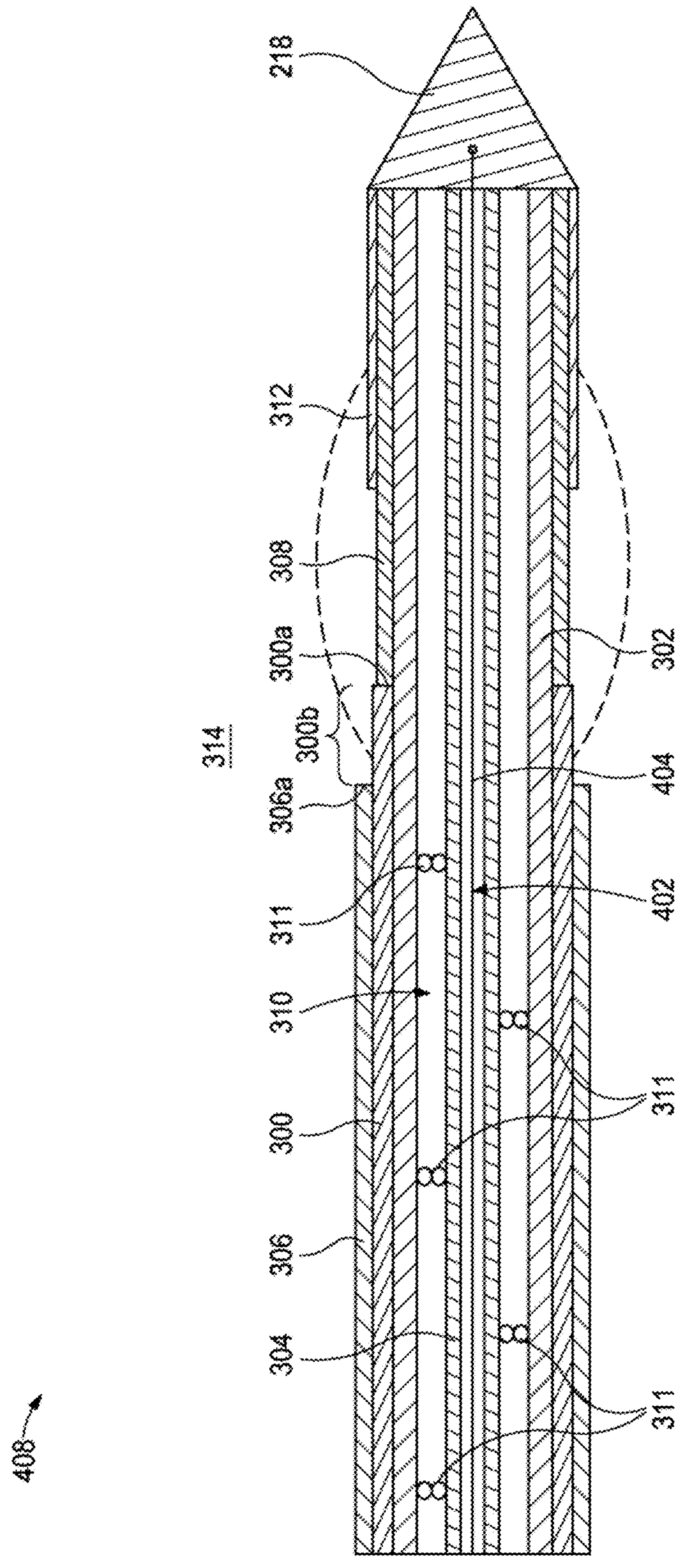
FIG. 4 is an enlarged, cross-sectional view of an alternative antenna for use with the ablation probe of FIG. 2, according to at least one aspect of the present disclosure.

FIG. 4 is an enlarged, cross-sectional view of an alternative antenna 408 that may be used with the ablation probe 104 of FIG. 2, according to at least one aspect of the present disclosure. The antenna 408 may be similar in some respects, such as structure and function, to the antenna 208 as described above, and therefore may be best understood with reference thereto.

Unlike the antenna 208, however, the inner conductor 304 may comprise tubular structure that defines a conduit 402 that extends therethrough. A wire 404 may extend from the cable assembly 206 (FIG. 2), through the conduit 402, and terminate at the stylet 218. The wire 404 may serve as a part of the RF supply path in lieu of the inner conductor 304. For instance, based on the antenna 408 being placed in the "RF" mode, the RF generator 130 (FIG. 1) may provide RF energy to the stylet 218 and the electrode 312 via the switch 134 and the wire 404. The wire 404 may be an insulated wire. Accordingly, with the addition of the antenna 408, the inner conductor 304 may serve to transmit microwave energy, while the wire 404 simultaneously serves to transmit RF energy.

The antennas 208, 408 may be configured to provide monopolar RF energy to tissue as opposed to bipolar RF energy. For instance, in some embodiments, the distal end 306*a* of the first insulation tube 306 may extend to, or beyond, the distal end 300*a* of the outer conductor 300 such that the antennas 208, 408 do not include the exposed portion 300*b*, thereby removing the return path for bipolar RF energy (e.g., the outer conductor 300). Accordingly, in such embodiments, the system 100 may include a return pad that may engage the patient and serve as the return path for the transmitted RF energy.

Figure 5:
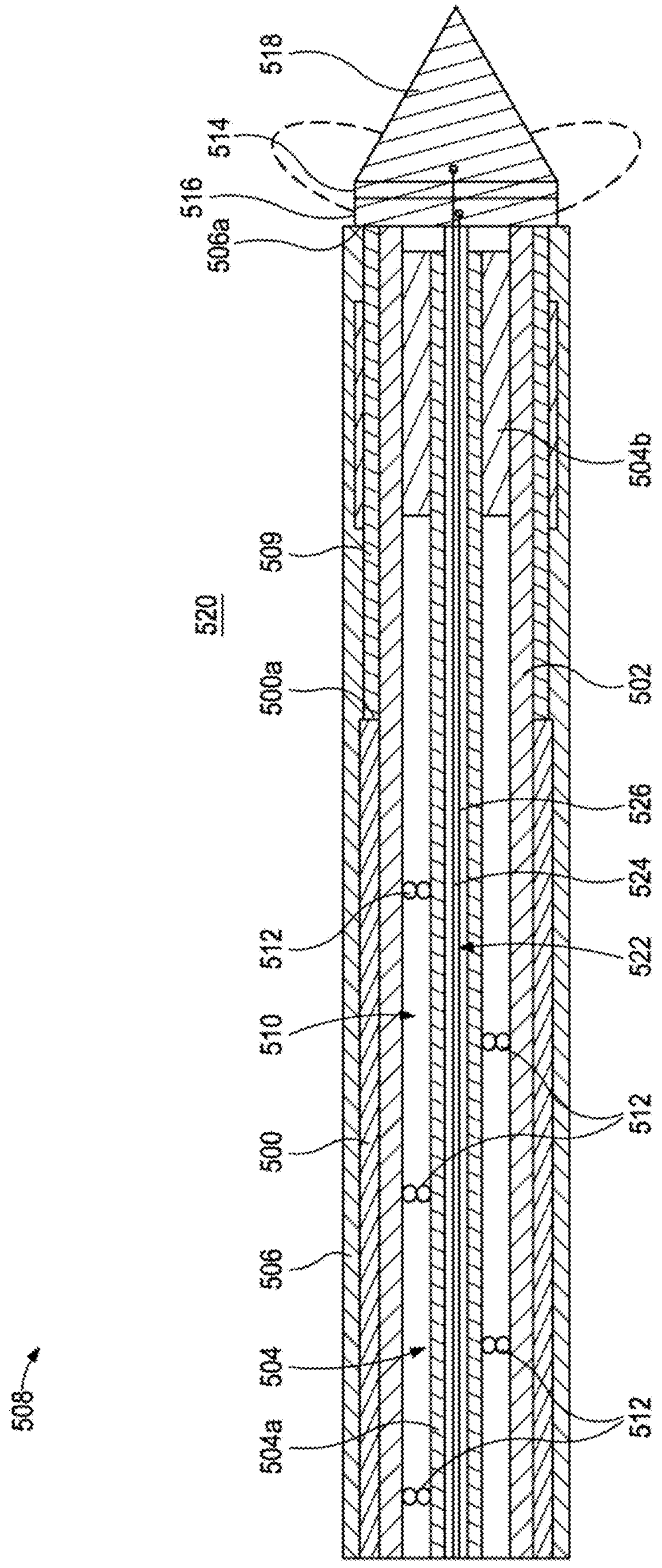
FIG. 5 is an enlarged, cross-sectional view of an alternative antenna for use with the ablation probe of FIG. 2, according to at least one aspect of the present disclosure.

FIG. 5 is an enlarged, cross-sectional view of an alternative antenna 508 that may be used with the ablation probe 104 of FIG. 2, according to one or more additional embodiments of the present disclosure. The antenna 508 may be similar in some respects to the antennas 208, 408 as described above, and therefore may be best understood with reference thereto.

The antenna 508 may include an outer conductor 500, a dielectric tube 502 extending within an interior of the outer conductor 500, and an inner conductor 504 extending within an interior of the dielectric tube 502. The outer conductor 500, the dielectric tube 502, and the inner conductor 504 may be similar in some respects to the outer conductor 300 (FIG. 3), the dielectric tube 302 (FIG. 3), and the inner conductor 304 (FIG. 3), respectively.

The antenna 508 may further include a first insulation tube 506 positioned about (around) the outer conductor 500. As illustrated, the distal end 506*a* of the first insulation tube 506 extends distally beyond the distal end 500*a* of the outer conductor 500 and to a stylet 518, which may be similar to the stylet 218 (FIG. 2). The antenna 508 may further include a second insulation tube 509 extending from the distal end 300*a* of the outer conductor 300 to the stylet 518 and may be positioned about (around) the dielectric tube 502.

As illustrated, an air gap 510 may be defined between the dielectric tube 502 and the inner conductor 504 and one or more spacers 512, similar to the spacers 311 (FIG. 3), may be positioned in the air gap 510 to maintain a known spacing between the dielectric tube 502 and the inner conductor 504.

The inner conductor 504 may comprise a tubular structure that defines a conduit 522 that extends therethrough. A first or "supply" wire 524 may extend from the cable assembly 206, through the conduit 522, and terminate at the stylet 518. The first wire 524 may serve as a part of an RF supply path, as will be discussed in more detail below. Moreover, the supply wire 524 may be an insulated wire.

The inner conductor 504 may include a conductor shaft 504*a* (first portion) and a conductor load 504*b* (second portion) extending distally from the conductor shaft 504*a*. The conductor shaft 504*a* may define, or exhibit, a first diameter and the conductor load 504*b* may define, or exhibit, a second diameter which is different (greater) than the first diameter. In some embodiments, the conductor shaft 504*a* and the conductor load 504*b* are integrally constructed (formed), such as on a lathe from a piece of stock metal. In such embodiments, the conductor shaft 504*a* and the conductor load 504*b* may be made of the same material including, but not limited to, stainless steel, silver, copper, brass or aluminum, alloys thereof, or any combination thereof. In other embodiments, however, the conductor shaft 504*a* and the conductor load 504*b* may be separate component parts that are operatively coupled (e.g., welded, mechanically fastened, etc.). In such embodiments, the material of the conductor shaft 504*a* and conductor load 504*b* may be the same or different. As one example, the conductor shaft 504*a* may be made of copper and the conductor load 504*b* may be made of brass.

The conductor load 504*b* may serve as a load point and may include a longitudinal length that is tuned to match the dielectric properties of the surrounding tissue, which may contribute to the ability of the antenna 508 to generate a spherical ablation zone, which may be more preferred than a typical ellipsoid or "tear drop" shaped ablation zone. More details regarding spherical ablation zones are provided in U.S. patent application Ser. No. 18/810,315, titled "COOLED ANTENNAS FOR SPHERICAL ABLATION", filed Aug. 20, 2024, which was previously incorporated by reference in its entirety herein.

The antenna 508 may further include an electrode 516 axially interposing the stylet 518 and the first and second insulator tubes 506, 509 and the dielectric tube 502. Moreover, an insulator 514 may axially interpose the electrode 516 and the stylet 518. A second or "return" wire 526 may extend from the cable assembly 206, through the conduit 522, and terminate at the electrode 516. The return wire 526 may serve as a part of an RF return path, as will be discussed in more detail below. Moreover, the return wire 526 may be an insulated wire.

Similar to the antenna 208 (FIG. 2), the antenna 508 is configured to deliver microwave or RF energy to tissue. The antenna 508 may be used in a first or "microwave" mode in which the antenna 508 provides microwave energy to tissue to generate a microwave ablation zone 210 (FIG. 2). More specifically, with reference to FIGS. 1, 2, and 5, when a user desires to provide microwave energy to tissue, the user may provide a first input to the controller 114 via the GUI 120. Based on receiving the first input, the controller 114 may place the switch 134 in the microwave state, as discussed elsewhere herein.

A user may then provide a second input to the controller 114 via the GUI 120. Based on receiving the second input, the controller 114 may cause the microwave generator 132 to provide microwave energy to the inner conductor 504 via the switch 134. The microwave energy may be delivered along the inner conductor 504 and may be emitted from the conductor shaft 504*a* and/or conductor load 504*b*, thereby generating the microwave ablation zone 210.

The antenna 508 may also be used in a second or "RF" mode in which the antenna 508 provides bipolar RF energy to tissue to generate an RF ablation zone 211 (FIG. 2). More specifically, and with continued reference to FIGS. 1, 2, and 5, a user may desire to provide bipolar RF energy to tissue, such as after providing microwave energy to tissue, as described above. To accomplish this, a user may provide a third input to the controller 114 via the GUI 120. Based on receiving the third input, the controller 114 may transition the switch 134 from the microwave state to the RF state, as discussed elsewhere herein.

A user may then provide a fourth input to the controller 114 via the GUI 120. Based on receiving the fourth input, the controller 114 may cause the RF generator 130 to provide RF energy to the stylet 518 via the switch 134 and the supply wire 524. The RF energy may then be delivered to the electrode 516 via tissue 520 surrounding the antenna 508, as shown with the dashed lines extending between the stylet 518 and the electrode 516 in FIG. 5. The RF energy may then be delivered along the return wire 526 as a return path. Accordingly, the foregoing bipolar RF energy delivery produces (generates) the RF ablation zone 211.

Accordingly, a user can selectively apply RF and microwave energy to patient tissue by simply switching the antenna 508 back and forth between the RF and microwave modes, such as by providing an input to the GUI 120 to transition the switch 134 between the RF and microwave states, respectively. It should be understood that the antenna 508 can be transitioned back and forward between the microwave and RF modes as desired by the user.

The above-described antennas 208, 408, 508 enable a user to selectively provide RF or microwave tissue to a patient with a single ablation probe. The combination of both energy modalities on a single probe may allow a physician to treat a variety of targets in a single case without having to change devices intraoperatively. For instance, during laparoscopic ablation, the physician could treat a large tumor with microwave ablation, control bleeding with RF ablation, and touch up other small exophytic nodules with RF ablation. The ability to provide RF energy also enables quick and fully tip encompassing cauterization if the stylet needs to be repositioned, track cautery during probe removal, or to perform functions similar to a Bovie cautery tool. A combination microwave and RF energy device may also improve the size of the ablation treatment and overcome ablation treatment issues of RF devices due to desiccated, non-conductive tissue. The antennas may be placed in the "RF" mode for more precise, localized heating and the "microwave" mode when large volume treatment zones are desired.

Embodiments Disclosed Herein Include

A. An energy delivery device comprising an antenna operable in a first mode in which the antenna provides microwave energy to tissue and a second mode in which the antenna provides radiofrequency (RF) energy to tissue.

B. A system comprising an energy delivery device comprising an antenna, a switch, and a controller to operably communicate with the switch, a microwave generator, and an RF generator. The switch is transitionable between a first state in which the switch electrically connects a microwave generator to the energy delivery device and electrically disconnects an RF generator from the energy delivery device and a second state, in which the switch electrically connects the RF generator to the energy delivery device and electrically disconnects the microwave generator from the energy delivery device. The controller is operable to place the switch in the first state, provide microwave energy to the energy delivery device via the microwave generator based on the switch being in the first state, transition the switch from the first state to the second state, and provide RF energy to the energy delivery device via the RF generator based on the switch being in the second state.

C. A non-transitory computer-readable medium storing instructions that, when executed by a processor, cause the processor to place a switch into a first state, wherein, in the first state, the switch electrically connects a microwave generator to an energy delivery device comprising an antenna and electrically disconnects an RF generator from the energy delivery device, control the microwave generator to provide microwave energy to the energy delivery device, transition the switch from the first state to a second state, wherein, in the second state, the switch electrically connects the RF generator to the energy delivery device and electrically disconnects the microwave generator from the energy delivery device, and control the RF generator to provide RF energy to the energy delivery device.

Each of embodiments A-C may have one or more of the following additional elements in any combination: Element 1: wherein the antenna comprises an inner conductor and an outer conductor surrounding the inner conductor, and wherein, in the second mode, the outer conductor serves as a portion of a return path for the RF energy. Element 2: further comprising a stylet arranged at a distal end of the antenna and extending distally from the inner conductor, wherein, in the second mode, the stylet serves as a portion of a supply path for the RF energy. Element 3: further comprising an electrode extending proximally from the stylet, wherein, in the second mode, the stylet and the electrode both serve as the portion of the supply path for the RF energy. Element 4: further comprising an insulation tube extending between the outer conductor and the stylet, wherein the electrode is positioned about the insulation tube. Element 5: wherein, in the second mode, the inner conductor and the stylet serve as a portion of the supply path for the RF energy. Element 6: wherein the inner conductor defines a conduit therethrough, the energy delivery device further comprising a wire extending through the conduit and in electrical communication with the stylet, wherein, in the second mode, the wire and the stylet both serve as the portion of the supply path for the RF energy. Element 7: further comprising an insulation tube surrounding the outer conductor, wherein a distal end of the insulation tube is positioned proximal to a distal end of the outer conductor such that a portion of the outer conductor is exposed. Element 8: wherein the antenna comprises a stylet, an electrode arranged proximal to the stylet, and an insulator interposing the electrode and the stylet, wherein, in the second mode the stylet serves as a portion of a supply path for the RF energy and the electrode serves as a portion of a return path for the RF energy. Element 9: wherein the antenna further comprises an inner conductor defining a conduit therethrough, a first wire extending through the conduit and in electrical communication with the stylet, wherein, in the second mode, the stylet and the first wire both serve as the portion of the supply path for the RF energy, and a second wire extending through the conduit and in electrical communication with the electrode, wherein, in the second mode, the electrode and the second wire both serve as the portion of the return path for the RF energy. Element 10: wherein the inner conductor comprises a conductor shaft exhibiting a first diameter and a conductor load extending from the conductor shaft and exhibiting a second diameter greater than the first diameter. Element 11: wherein the antenna comprises an inner conductor, an outer conductor surrounding the inner conductor, and a stylet extending distally from the inner conductor, wherein, in the second state, the stylet serves as a portion of a supply path for the RF energy and the outer conductor serves as a portion of a return path for the RF energy. Element 12: wherein the antenna further comprises an electrode extending proximally from the stylet, wherein, in the second state, the stylet and the electrode both serve as the portion of the supply path for the RF energy. Element 13: wherein, in the second state, the inner conductor and the stylet both serve as the portion of the supply path for the RF energy. Element 14: wherein the inner conductor defines a conduit therethrough and the energy delivery device further comprises a wire extending through the conduit and in electrical communication with the stylet, and wherein, in the second state, the wire and the stylet both serve as the portion of the supply path for the RF energy. Element 15: wherein the energy delivery device further comprises an insulation tube surrounding the outer conductor, and wherein a distal end of the insulation tube is positioned proximal to a distal end of the outer conductor such that a portion of the outer conductor is exposed. Element 16: wherein the antenna comprises a stylet, an electrode arranged proximal to the stylet, and an insulator interposing the electrode and the stylet, wherein, in the second state, the stylet serves as a portion of a supply path for the RF energy and the electrode serves as a portion of a return path for the RF energy. Element 17: wherein the antenna further comprises an inner conductor defining a conduit therethrough, a first wire extending through the conduit and in electrical communication with the stylet, wherein, in the second state, the stylet and the first wire both serve as the portion of the supply path for the RF energy, and a second wire extending through the conduit and in electrical communication with the electrode, wherein, in the second state, the electrode and the second wire both serve as the portion of the return path for the RF energy.

By way of non-limiting example, exemplary combinations applicable to A, B, and C include: Element 1 with Element 2; Element 1 with Elements 2 and 3; Element 1 with Elements 2-4; Element 1 with Elements 2 and 5; Element 1 with Elements 2 and 6; Element 1 with Element 7; Element 1 with Element 8; Element 1 with Elements 8 and 9; Element 1 with Elements 8-10; Element 8 with Element 9; Element 8 with Elements 9 and 10; Element 11 with Element 12; Element 11 with Element 13; Element 11 with Element 14; Element 11 with Element 15; Element 11 with Element 16; Element 11 with Elements 16 and 17; Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, and the like are used in relation to the illustrative embodiments as they are depicted in the figures, the upward direction being toward the top of the corresponding figure and the downward direction being toward the bottom of the corresponding figure.

What is claimed is:

1. An energy delivery device, comprising:

an antenna operable in:

a first mode in which the antenna provides microwave energy to tissue; and a second mode in which the antenna provides radiofrequency (RF) energy to tissue, wherein the antenna comprises:

a stylet;

an electrode arranged proximal to the stylet;

an insulator interposed between the electrode and the stylet;

an inner conductor defining a conduit therethrough;

a first wire extending through the conduit and in electrical communication with the stylet, such that in the second mode the stylet and the first wire serve as a portion of a supply path for the RF energy; and a second wire extending through the conduit and in electrical communication with the electrode, such that in the second mode the electrode and the second wire serve as a portion of a return path for the RF energy.

2. The energy delivery device of claim 1, wherein the antenna further comprises an outer conductor surrounding the inner conductor.

3. The energy delivery device of claim 2, further comprising an insulation tube extending between the outer conductor and the stylet, wherein the electrode is positioned about the insulation tube.

4. The energy delivery device of claim 2, further comprising an insulation tube surrounding the outer conductor, wherein a distal end of the insulation tube is positioned proximal to a distal end of the outer conductor such that a portion of the outer conductor is exposed.

5. The energy delivery device of claim 2, wherein the inner conductor comprises:

a conductor shaft exhibiting a first diameter; and a conductor load extending from the conductor shaft and exhibiting a second diameter greater than the first diameter.

6. A system, comprising:

an energy delivery device including an antenna;

a switch, transitionable between:

a first state, in which the switch electrically connects a microwave generator to the energy delivery device and electrically disconnects an RF generator from the energy delivery device; and a second state, in which the switch electrically connects the RF generator to the energy delivery device and electrically disconnects the microwave generator from the energy delivery device; and a controller to operably communicate with the switch, the microwave generator, and the RF generator, wherein the controller is operable to:

place the switch in the first state;

provide microwave energy to the energy delivery device via the microwave generator based on the switch being in the first state;

transition the switch from the first state to the second state; and provide RF energy to the energy delivery device via the RF generator based on the switch being in the second state, wherein the antenna comprises:

a stylet;

an electrode arranged proximal to the stylet;

an insulator interposed between the electrode and the stylet;

an inner conductor defining a conduit therethrough;

a first wire extending through the conduit and in electrical communication with the stylet, such that in the second mode the stylet and the first wire serve as a supply path for the RF energy; and a second wire extending through the conduit and in electrical communication with the electrode, such that in the second mode the electrode and the second wire serve as a return path for the RF energy.

7. The system of claim 6, wherein the antenna further comprises an outer conductor surrounding the inner conductor.

8. The system of claim 7, wherein the energy delivery device further comprises an insulation tube surrounding the outer conductor, and wherein a distal end of the insulation tube is positioned proximal to a distal end of the outer conductor such that a portion of the outer conductor is exposed.

* * * * *